(12) United States Patent
Shea et al.

(10) Patent No.: US 7,220,573 B2
(45) Date of Patent: May 22, 2007

(54) ARRAY ASSAY DEVICES AND METHODS OF USING THE SAME

(75) Inventors: Lawrence R. Shea, Charlotte, NC (US); Douglas G. Summers, Sunnyvale, CA (US); Richard O. Hilson, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 95 days.

(21) Appl. No.: 10/177,358

(22) Filed: Jun. 21, 2002

(65) Prior Publication Data

US 2003/0235825 A1    Dec. 25, 2003

(51) Int. Cl.
*C07H 21/04* (2006.01)
*C12Q 1/68* (2006.01)

(52) U.S. Cl. .................. 435/287.2; 435/6; 435/91.1; 435/287.1

(58) Field of Classification Search ............. 435/287.2, 435/6, 288.3, 288.4; 536/23.1, 24.3
See application file for complete search history.

(56) References Cited

U.S. PATENT DOCUMENTS

| | | | | |
|---|---|---|---|---|
| 3,584,598 | A | * | 6/1971 | Gayle et al. ............... 116/308 |
| 4,126,224 | A | * | 11/1978 | Laauwe et al. ............. 206/540 |
| 4,318,477 | A | * | 3/1982 | Kerpe ........................ 206/534 |
| 4,857,453 | A | | 8/1989 | Ullman et al. |
| 4,981,786 | A | | 1/1991 | Dafforn et al. |
| RE399,134 | | * | 10/1998 | Lidle, Jr. |
| 5,945,334 | A | * | 8/1999 | Besemer et al. .......... 435/287.2 |
| 5,959,098 | A | * | 9/1999 | Goldberg et al. ........... 536/25.3 |
| 6,037,168 | A | | 3/2000 | Brown |
| 6,225,109 | B1 | * | 5/2001 | Juncosa et al. ........... 435/288.5 |
| 6,258,593 | B1 | * | 7/2001 | Schembri et al. ........ 435/287.2 |
| 6,391,541 | B1 | | 5/2002 | Petersen et al. |
| 6,555,361 | B1 | * | 4/2003 | Lyman et al. ............ 435/287.2 |
| 2001/0046702 | A1 | * | 11/2001 | Schembri ................. 435/287.2 |

FOREIGN PATENT DOCUMENTS

| | | | |
|---|---|---|---|
| WO | WO 95/27196 | * | 10/1995 |
| WO | WO 00/20862 | | 4/2000 |
| WO | WO 00/73766 | | 12/2000 |

OTHER PUBLICATIONS

Ahern (The Scientist, vol. 9, No. 15, p. 20, Jul. 1995).*
European Patent Office Communication dated Sep. 29, 2003, Search Report and Annex for EP Application No. 03253935 dated Sep. 19, 2003, counterpart of U.S. Appl. No. 10/177,358.

* cited by examiner

*Primary Examiner*—Jeanine Anne Goldberg

(57) ABSTRACT

Array assay devices and methods for using the same in array based assays are provided. The subject devices are characterized by having a base dimensioned to hold a substrate having at least one array, a cover dimensioned to cover the substrate and a snap-fit for holding the cover and the base together to enclose a space between the base and the cover. The subject invention also includes methods for performing an array assay. In the subject methods, a subject device is provided and a substrate having at least one array is positioned on the base. The snap-fit is engaged to hold the cover and the base together to enclose a space between the base and the cover. Next, a sample is contacted with the at least one array and an array assay is performed. The subject invention also includes kits which include the subject devices.

20 Claims, 8 Drawing Sheets

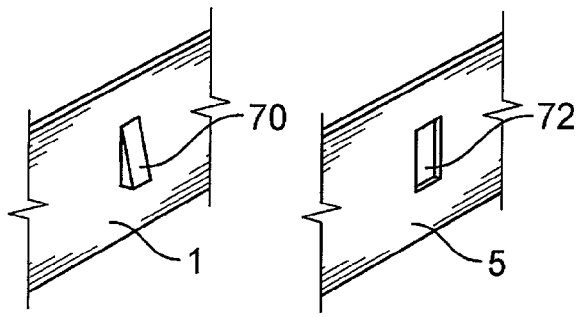
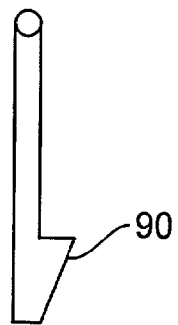
FIG. 8  FIG. 9A
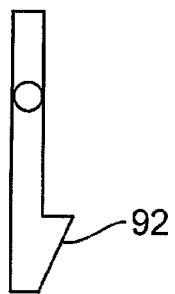
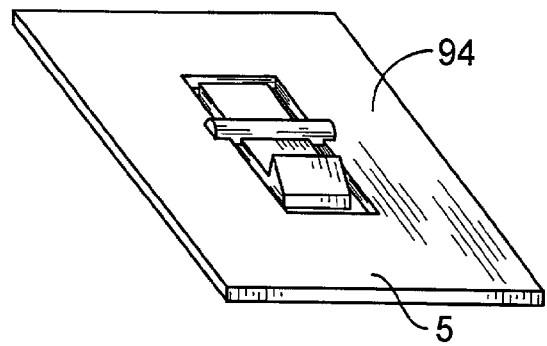
FIG. 9B  FIG. 9C
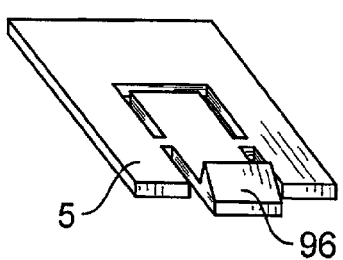
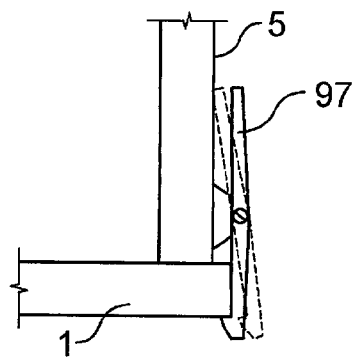
FIG. 9D  FIG. 9E

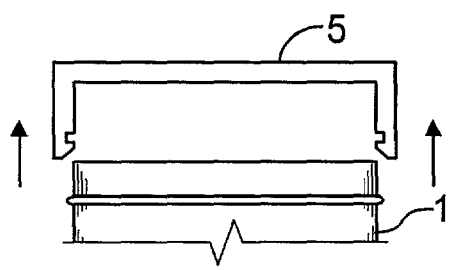
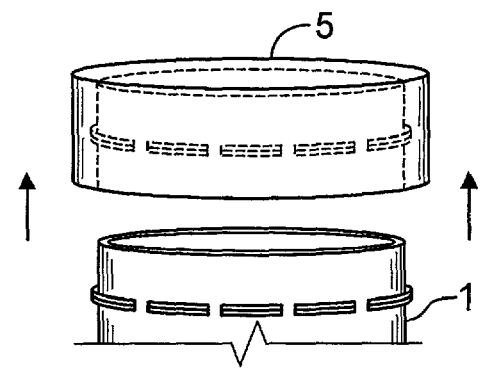
FIG. 10A
FIG. 10B
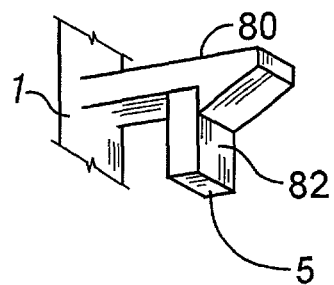
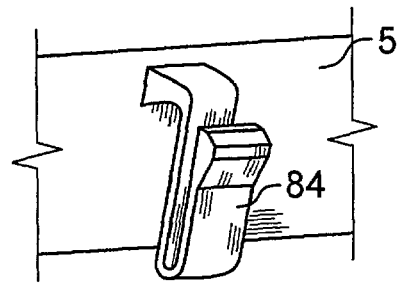
FIG. 11A
FIG. 11B
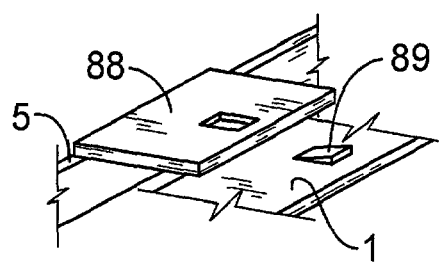
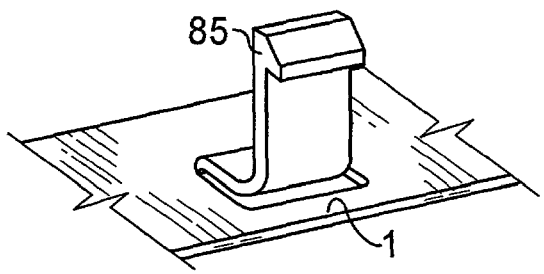
FIG. 11C
FIG. 11D

ARRAY ASSAY DEVICES AND METHODS OF USING THE SAME

FIELD OF THE INVENTION

The field of this invention is biopolymeric arrays.

BACKGROUND OF THE INVENTION

Array assays between surface bound binding agents or probes and target molecules in solution may be used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the substrate, covered with another substrate to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag, chemiluminescent tag or radioactive tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As will be apparent, control of the assay environment and conditions contributes to increased reliability and reproducibility of the array assays. However, merely placing a slide over the substrate or positioning a cover slip over the substrate, as is commonly done, is often insufficient to allow precise control over the assay and is labor intensive as well.

During an array assay such as a hybridization assay, the assay is often performed at elevated temperatures and care must be taken so that the array does not dry out. Using a second slide positioned over the substrate allows contents to leak and/or evaporate which can result in the array drying out during use, adversely impacting the assay. In addition, the substrate cannot be tipped or moved from the horizontal position without risk that the substrate or cover slip will slip off. Maintaining the array in a humid environment may reduce drying-out, but offers only an incomplete solution.

Various chambers or containers have been developed to eliminate the use of a substrate or cover slip and facilitate the above described array assays. However, while many of these chambers are effective, they often require the user to manually assemble the apparatus around an array using screws to maintain the structure together. Such procedures take time and may introduce contaminants into the array due to the increased handling thereof during assembly of the apparatus.

Thus, there continues to be an interest in the development of new devices for array-based hybridizations and methods of using the same. Of particular interest is the development of an array assay device, and methods of use thereof, that is easy to assemble and use, includes minimal components, prevents drying out of the array and that may also be capable of testing multiple samples with multiple arrays without cross contamination.

SUMMARY OF THE INVENTION

Array assay devices and methods for using the same in array based assays are provided. The subject devices are characterized by having a base dimensioned to hold a substrate having at least one array, a cover dimensioned to cover the substrate and a snap-fit for holding the cover and the base together to enclose a space between the base and the cover. The subject invention also includes methods for performing an array assay. In the subject methods, a subject device is provided and a substrate having at least one array is positioned on the base. The snap-fit is engaged to hold the cover and the base together to enclose a space between the base and the cover. Next, a sample is contacted with the at least one array and an array assay is performed. The subject invention also includes kits which include the subject devices.

BRIEF DESCRIPTIONS OF THE DRAWINGS

FIG. 8 shows an exemplary embodiment of a planar snap-fit according to the subject invention.

FIGS. 9A-9E show exemplary embodiments of torsion snap-fits according to the subject invention.

FIGS. 10A-10B show exemplary embodiments of annular snap-fits according to the subject invention.

FIGS. 11A-11D show exemplary embodiments of cantilever snap-fits according to the subject invention.

DEFINITIONS

Figure 1:
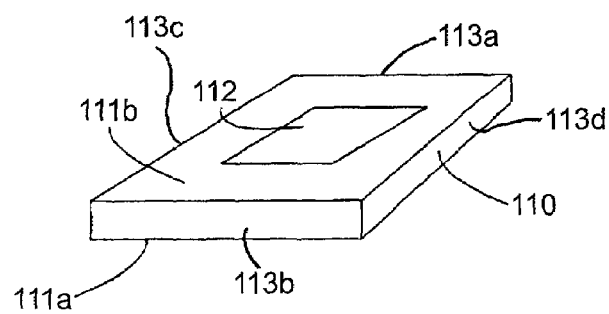
FIG. 1 shows an exemplary substrate carrying an array, such as may be used in the devices of the subject invention.

The term "polymer" refers to any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "monomer" as used herein refers to a chemical entity that can be covalently linked to one or more other such entities to form an oligomer. Examples of "monomers" include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). The initial substrate-bound monomer is generally used as a building-block in a multistep synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably. Examples of oligomers and polymers include polydeoxyribonucleotides, polyribonucleotides, other polynucleotides which are—or C-glycosides of a purine or pyrimidine base, polypeptides, polysaccharides, and other chemical entities that contain repeating units of like chemical structure.

The term "ligand" as used herein refers to a moiety that is capable of covalently or otherwise chemically binding a compound of interest. The ligand may be a portion of the compound of interest. The term "ligand" in the context of the invention may or may not be an "oligomer" as defined above. The term "ligand" as used herein may also refer to a compound that is synthesized on the substrate surface as well as a compound is "pre-synthesized" or obtained commercially, and then attached to the substrate surface.

The terms "array" "biopolymeric array" and "biomolecular array" are used herein interchangeably to refer to an arrangement of ligands or molecules of interest on a substrate surface which can be used for analyte detection, combinatorial chemistry, or other applications wherein a two-dimensional arrangement of molecules of interest can be used. That is, the terms refer to an ordered pattern of probe molecules adherent to a substrate, i.e., wherein a plurality of molecular probes are bound to a substrate surface and arranged in a spatially defined and physically addressable manner. Such arrays may be comprised of oligonucleotides, peptides, polypeptides, proteins, antibodies, or other molecules used to detect sample molecules in a sample fluid.

The term "biomolecule" means any organic or biochemical molecule, group or species of interest which may be formed in an array on a substrate surface. Exemplary biomolecules include peptides, proteins, amino acids and nucleic acids.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA"s used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "chemically inert" is used herein to mean substantially unchanged chemically by contact with reagents and conditions normally involved in hybridization reactions or any other related reactions, e.g., proteomic array applications.

The term "communicating" information refers to transmitting data representing that information as electrical signals over a suitable communication channel (for example, a private or public network).

The term "forwarding" an item refers to any means of getting that item from one location to the next, whether by physically transporting that item or otherwise (where that is possible) and includes, at least in the case of data, physically transporting a medium carrying the data or communicating the data.

The term "physically inert" is used herein to mean substantially unchanged physically by contact with reagents and conditions normally involved in hybridization reactions or any other related reactions.

The terms "target" "target molecule" and "analyte" are used herein interchangeably and refer to a known or unknown molecule in a sample, which will hybridize to a molecular probe on a substrate surface if the target molecule and the molecular probe contain complementary regions, i.e., if they are members of a specific binding pair. In general, the target molecule is a biopolymer, i.e., an oligomer or polymer such as an oligonucleotide, a peptide, a polypeptide, a protein, and antibody, or the like.

The term "hybridization" as used herein refers to binding between complementary or partially complementary molecules, for example as between the sense and anti-sense strands of double-stranded DNA. Such binding is commonly non-covalent binding, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "hybridization solution" or "hybridization reagent" used herein interchangeably refers to a solution suitable for use in a hybridization reaction.

The terms "mix" and "mixing" as used herein means to cause fluids to flow within a volume so as to more uniformly distribute solution components, as after different solutions are combined or after a solution is newly introduced into a volume or after a component of the solution is locally depleted.

The term "probe" as used herein refers to a molecule of known identity adherent to a substrate.

The term "remote location" refers to a location other than the location at which the array is present and hybridization occur. As such, when one item is indicated as being "remote" from another, what is meant is that the two items are at least in different buildings, and may be at least one mile, ten miles, or at least one hundred miles apart.

The term "sealing element" is used herein to refer to any sealing device or structure that produces a seal between two surfaces, such as a gasket, a lip, ledge or ridge, material interface, viscous sealant, or the like.

The term "substantially vapor and fluid tight" or "substantially vapor and fluid tight seal" used herein interchangeably means any seal that is produced by any sealing element or structure that prevents substantial evaporation of fluidic contents from an area bounded by the seal, e.g., from an assay area bounded by the sealing element.

the term "substrate" as used herein refers to a surface upon which marker molecules or probes, e.g., an array, may be adhered. Glass slides are the most common substrate for biochips, although fused silica, silicon, plastic and other materials are also suitable.

The term "surfactant" is used herein in its conventional sense to refer to a compound effective to reduce surface tension in a fluid and improve wetting of surfaces. Suitable surfactants herein include anionic, cationic, amphoteric and nonionic surfactants, with anionic surfactants and polymeric nonionic surfactants being preferred in certain embodiments.

The term "thermally stable" is used herein to mean substantially unchanged, i.e., does not degrade or otherwise chemically react at temperatures used for hybridization reactions.

The term "snap-fit" or "snap-fit attachment", used herein interchangeably, are used herein to refer to any suitable "built in" or integral latching or attachment feature or mechanism for attaching one part or one element to another. In the context of the subject invention, a snap fit or snap fit feature is used to join and retain a subject base and a subject cover in a closed configuration. A snap-fit attachment differs from loose or chemical attachment methods. A snap-fit requires no additional pieces, materials or tools to carry out the function of attachment. Representative snap-fits suitable for use with the present invention are described in Bonenberger, P., The First Snap-Fit Handbook, Hanzer (2000), incorporated herein in its entirety, and include, but are not limited to, planar snap-fit, cantilever snap-fit, torsion snap-fit and annular snap-fit.

The term "stringent hybridization conditions" as used herein refers to conditions that are that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

DETAILED DESCRIPTION OF THE INVENTION

Array assay devices and methods for using the same in array based assays are provided. The subject devices are characterized by having a base dimensioned to hold a substrate having at least one array, a cover dimensioned to cover the substrate and a snap-fit for holding the cover and the base together to enclose a space between the base and the cover. The subject invention also includes methods for performing an array assay. In the subject methods, a subject device is provided and a substrate having at least one array is positioned on the base. The snap-fit is engaged to hold the cover and the base together to enclose a space between the base and the cover. Next, a sample is contacted with the at least one array and an array assay is performed. The subject invention also includes kits which include the subject devices.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a port" includes a plurality of such ports and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides devices and methods for performing array assays, i.e., array binding assays. The subject inventions can be used with a number of different types of arrays in which a plurality of distinct polymeric binding agents are stably associated with at least one surface of a substrate or solid support. The polymeric binding agents may vary widely, however polymeric binding agents of particular interest include peptides, proteins, nucleic acids, polysaccharides, synthetic mimetics of such biopolymeric binding agents, etc. In many embodiments of interest, the biopolymeric arrays are arrays of nucleic acids, including oligonucleotides, polynucleotides, cDNAs, mRNAs, synthetic mimetics thereof, and the like.

While the subject devices find use in array hybridization assays, the subject devices also find use in any suitable binding assays in which members of a specific binding pair interact. That is, any of a number of different binding assays may be performed with the subject devices, where typically a first member of a binding pair is stably associated with the surface of a substrate and a second member of a binding pair is free in a sample, where the binding members may be: ligands and receptors, antibodies and antigens, complementary nucleic acids, and the like. For ease of description only, the subject devices and methods described below will be described primarily in reference to hybridization assays by way of example only, where such examples are not intended to limit the scope of the invention. It will be appreciated by those of skill in the art that the subject devices and methods may be employed for use with other binding assays as well, such as immunoassays, proteomic, etc.

In further describing the subject invention, representative arrays used in the subject invention will be described first to provide a proper foundation for the subject invention. Next, devices employed in the subject invention are described in greater detail, followed by a detailed description of the subject methods and kits which include the subject devices.

Representative Biopolymeric Arrays

As mentioned above, the devices of the subject invention are used with arrays and more specifically biopolymeric arrays. Such biopolymeric arrays find use in a variety of applications, including gene expression analysis, drug screening, nucleic acid sequencing, mutation analysis, and the like. These biopolymeric arrays include a plurality of ligands or molecules or probes (i.e., binding agents or members of a binding pair) deposited onto the surface of a substrate in the form of an "array" or pattern.

The biopolymeric arrays include at least two distinct polymers that differ by monomeric sequence attached to different and known locations on the substrate surface. Each distinct polymeric sequence of the array is typically present as a composition of multiple copies of the polymer on a substrate surface, e.g., as a spot or feature on the surface of the substrate. The number of distinct polymeric sequences, and hence spots or similar structures, present on the array may vary, where a typical array may contain more than about ten, more than about one hundred, more than about one thousand, more than about ten thousand or even more than about one hundred thousand features in an area of less than about 20 $cm^2$ or even less than about 10 $cm^2$. For example, features may have widths (that is, diameter, for a round spot) in the range from about 10 μm to about 1.0 cm. In other embodiments, each feature may have a width in the range from about 1.0 μm to about 1.0 mm, usually from about 5.0 μm to about 500 μm and more usually from about 10 μm to about 200 μm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10% or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents, but may not be present when, for example, photolithographic array fabrication process are used. It will be appreciated though, that the interfeature areas, when present, could be of various sizes and configurations. The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

In the broadest sense, the arrays are arrays of polymeric or biopolymeric ligands or molecules, i.e., binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like.

The arrays may be produced using any convenient protocol. Various methods for forming arrays from pre-formed probes, or methods for generating the array using synthesis techniques to produce the probes in situ, are generally known in the art. See, for example, Southern, U.S. Pat. No. 5,700,637; Pirrung, et al., U.S. Pat. No. 5,143,854 and Fodor, et al. (1991) Science 251:767-777, the disclosures of which are incorporated herein by reference and PCT International Publication No. WO92/10092. For example, probes can either be synthesized directly on the solid support or substrate to be used in the array assay or attached to the substrate after they are made. Arrays may be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos: 6,242, 266, 6,232,072, 6,180,351, 6,171,797, and 6,323,043; and U.S. patent application Ser. No. 09/302,898 filed Apr. 30, 1999 by Caren et al., and the references cited therein, the disclosures of which are herein incorporated by reference. Other drop deposition methods may be used for fabrication. Also, instead of drop deposition methods, photolithographic array fabrication methods may be used such as described in U.S. Pat. Nos. 5,599,695, 5,753,788, and 6,329,143, the disclosures of which are herein incorporated by reference. As mentioned above, interfeature areas need not be present, particularly when the arrays are made by photolithographic methods as described in those patents.

A variety of solid supports or substrates may be used, upon which an array may be positioned. In certain embodiments, a plurality of arrays may be stably associated with one substrate. For example, a plurality of arrays may be stably associated with one substrate, where the arrays are spatially separated from some or all of the other arrays associated with the substrate.

The substrate may be selected from a wide variety of materials including, but not limited to, natural polymeric materials, particularly cellulosic materials and materials derived from cellulose, such as fiber containing papers, e.g., filter paper, chromatographic paper, etc., synthetic or modified naturally occurring polymers, such as nitrocellulose, cellulose acetate, poly (vinyl chloride), polyamides, polyacrylamide, polyacrylate, polymethacrylate, polyesters, polyolefins, polyethylene, polytetrafluoro-ethylene, polypropylene, poly (4-methylbutene), polystyrene, poly (ethylene terephthalate), nylon, poly(vinyl butyrate), cross linked dextran, agarose, etc.; either used by themselves or in conjunction with other materials; fused silica (e.g., glass), bioglass, silicon chips, ceramics, metals, and the like. For example, substrates may include polystyrene, to which short oligophosphodiesters, e.g., oligonucleotides ranging from about 5 to about 50 nucleotides in length, may readily be covalently attached (Letsinger et al. (1975) *Nucl. Acids Res.* 2:773-786), as well as polyacrylamide (Gait et al. (1982) *Nucl. Acids Res.* 10:6243-6254), silica (Caruthers et al. (1980) *Tetrahedron Letters* 21:719-722), and controlled-pore glass (Sproat et al. (1983) *Tetrahedron Letters* 24:5771-5774). Additionally, the substrate can be hydrophilic or capable of being rendered hydrophilic.

Suitable substrates may exist, for example, as sheets, tubing, spheres, containers, pads, slices, films, plates, slides, strips, disks, etc. The substrate is usually flat, but may take on alternative surface configurations. The substrate can be a flat glass substrate, such as a conventional microscope glass slide, a cover slip and the like. Common substrates used for the arrays of probes are surface-derivatized glass or silica, or polymer membrane surfaces, as described in Maskos, U. et al., *Nucleic Acids Res,* 1992, 20:1679-84 and Southern, E. M. et al., *Nucleic acids Res,* 1994, 22:1368-73.

Each array may cover an area of less than about 100 cm$^2$, or even less than about 50 cm$^2$, 10 cm$^2$ or 1 cm$^2$. In many embodiments, the substrate carrying the one or more arrays will be shaped generally as a rectangular solid (although other shapes are possible), having a length of more than about 4 mm and less than about 1 m, usually more than about 4 mm and less than about 600 mm, more usually less than about 400 mm; a width of more than about 4 mm and less than about 1 m, usually less than about 500 mm and more usually less than about 400 mm; and a thickness of more than about 0.01 mm and less than about 5.0 mm, usually more than about 0.1 mm and less than about 2 mm and more usually more than about 0.2 and less than about 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least about 20%, or about 50% (or even at least about 70%, 90%, or 95%), of the illuminating light incident on the substrate as may be measured across the entire integrated spectrum of such illuminating light or alternatively at 532 nm or 633 nm.

Immobilization of the probe to a suitable substrate may be performed using conventional techniques. See, e.g., Letsinger et al. (1975) *Nucl. Acids Res.* 2:773-786; Pease, A. C. et al., *Proc. Nat. Acad. Sci. USA,* 1994, 91:5022-5026. and "Oligonucleotide Synthesis, a Practical Approach," Gait, M. J. (ed.), Oxford, England: IRL Press (1984). The surface of a substrate may be treated with an organosilane coupling agent to functionalize the surface. See, e.g., Arkins, "Silane Coupling Agent Chemistry," *Petrarch Systems Register and Review,* Eds. Anderson et al. (1987) and U.S. Pat. No. 6,258,454.

Figure 2:
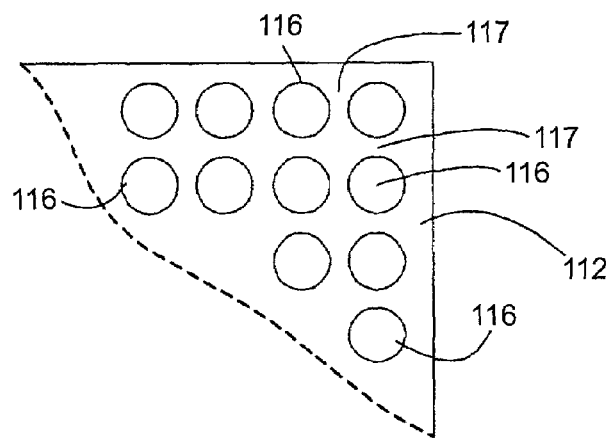
FIG. 2 shows an enlarged view of a portion of FIG. 1 showing spots or features.
Figure 3:
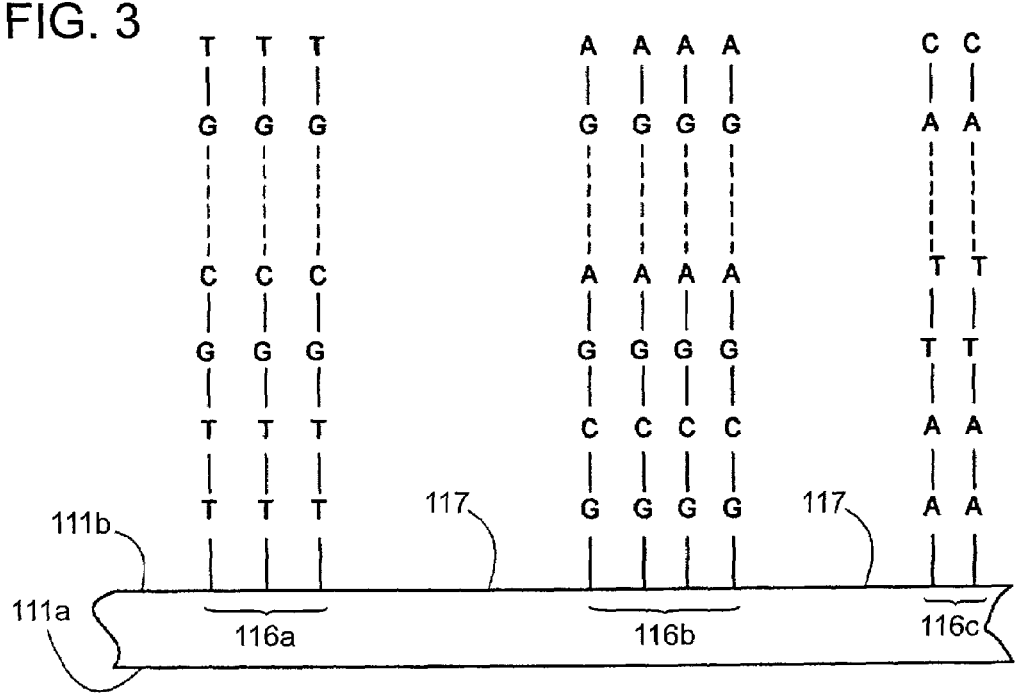
FIG. 3 shows an enlarged view of a portion of the substrate of FIG. 2.

Referring first to FIGS. 1-3, typically biopolymeric arrays of the present invention use a contiguous planar substrate 110 carrying an array 112 disposed on a rear surface 111b of substrate 110. It will be appreciated though, that more than one array (any of which are the same or different) may be present on rear surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111b, with regions of the rear surface 111b adjacent the opposed sides 113c, 113d and leading end 113a and trailing end 113b of slide 110, not being covered by any array 112. A front surface 111a of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of biopolymers, e.g., in the form of polynucleotides. As mentioned above, all of the features 116 may be different, or some or all could be the same. The interfeature areas 117 could be of various sizes and configurations. Each feature carries a predetermined biopolymer such as a predetermined polynucleotide (which includes the possibility of mixtures of polynucleotides). It will be understood that there may be a linker molecule (not shown) of any known types between the rear surface 111b and the first nucleotide.

Substrate 110 may carry on front surface 111a, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

Array Assay Devices

As summarized above, the array assay devices of the present invention are used with a substrate having at least one array thereon to perform an array assay procedure. Generally, the subject array assay devices include a base dimensioned to hold a substrate having at least one array, a cover dimensioned to cover the substrate and a snap-fit that enables the base and the cover to be held together to enclose a space between the base and the cover. The base and the cover may be two separate, i.e., completely separable, components or they may be secured together on one side, e.g., using a hinge or the like. The subject invention also includes a sealing element which provides a substantially vapor and fluid tight seal around an array on a substrate when the base and cover are snap-fit together to provide a substantially vapor and fluid tight assay area around the array. Where more than one array is present on a substrate, typically each array is surrounded or bounded by the sealing element which provides individual seals or individual assay areas around each array such that multiple samples may be tested with multiple arrays without cross contamination. The subject array assay devices usually also include at least one access port for the introduction and/or removal of fluids and/or gases from the array assay device.

The array assay devices of the subject invention may assume a variety of shapes raging from simple to complex, with the only limitation that they be suitably shaped to receive (i.e., retain or hold) at least one array therein. In many embodiments, the array assay devices will assume a circular, square, oblong, cylindrical, or rectangular shape, although other shapes are possible as well such as irregular or complex shapes. For example, in those embodiments where at least one array is stably associated with a substrate that is a microscope slide, e.g., a 1"×3" glass microscope slide as is known in the art, the array assay device may be similarly rectangularly shaped.

Similarly, the size of the array assay devices may vary depending on a variety of factors, including, but not limited to, the size of the array substrate and the like. Generally, the subject array assay devices will be dimensioned to retain a substrate having at least one array. Furthermore, the subject devices are sized to be easily transportable or moveable. In certain embodiments of the subject devices having a substantially rectangular shape, the length of such array assay devices typically ranges from about 10 mm to about 200 mm, usually from about 20 mm to about 150 mm and more usually from about 22 mm to about 100 mm, the width typically ranges from about 10 mm to about 100 mm, usually from about 20 mm to about 50 mm and more usually from about 22 mm to about 40 mm and the thickness typically ranges from about 4 mm to about 60 mm, usually from about 8 mm to about 40 mm and more usually from about 10 mm to about 30 mm. However, these dimensions are exemplary only and may vary as necessary.

Furthermore, the subject array assay devices may be manufactured from a variety of materials, with the only limitation being that the such materials used to fabricate the subject devices will not substantially interfere with the assay reagents, the assay and will have minimal non specific binding characteristics, e.g., substantially chemically inert, thermally stable, etc. Specifically, the materials should be chemically and physically stable under conditions employed for array assay. Examples of such materials may include, but are not limited to, plastics such as polytetrafluoroethylene, polypropylene, polystyrene, polycarbonate, PVC and blends thereof, elastomers, stainless steel and alloys thereof, siliceous materials, e.g., glasses, fused silica, ceramics and the like. The base and the cover may be made of the same or different materials. As will be apparent to those of skill in the art, the subject array assay devices or any component thereof may be manufactured to be reuseable or single use. That is, one or more components of the subject array assay devices may be reusable while other components may be single use. For example, the subject devices may include a substrate receiving frame and/or an array holder which will be described in greater detail below, where the array receiving frame and/or array holder may be single use or disposable while the array assay device, i.e., the base and the cover, may be reusable or vice versa.

Figure 4:
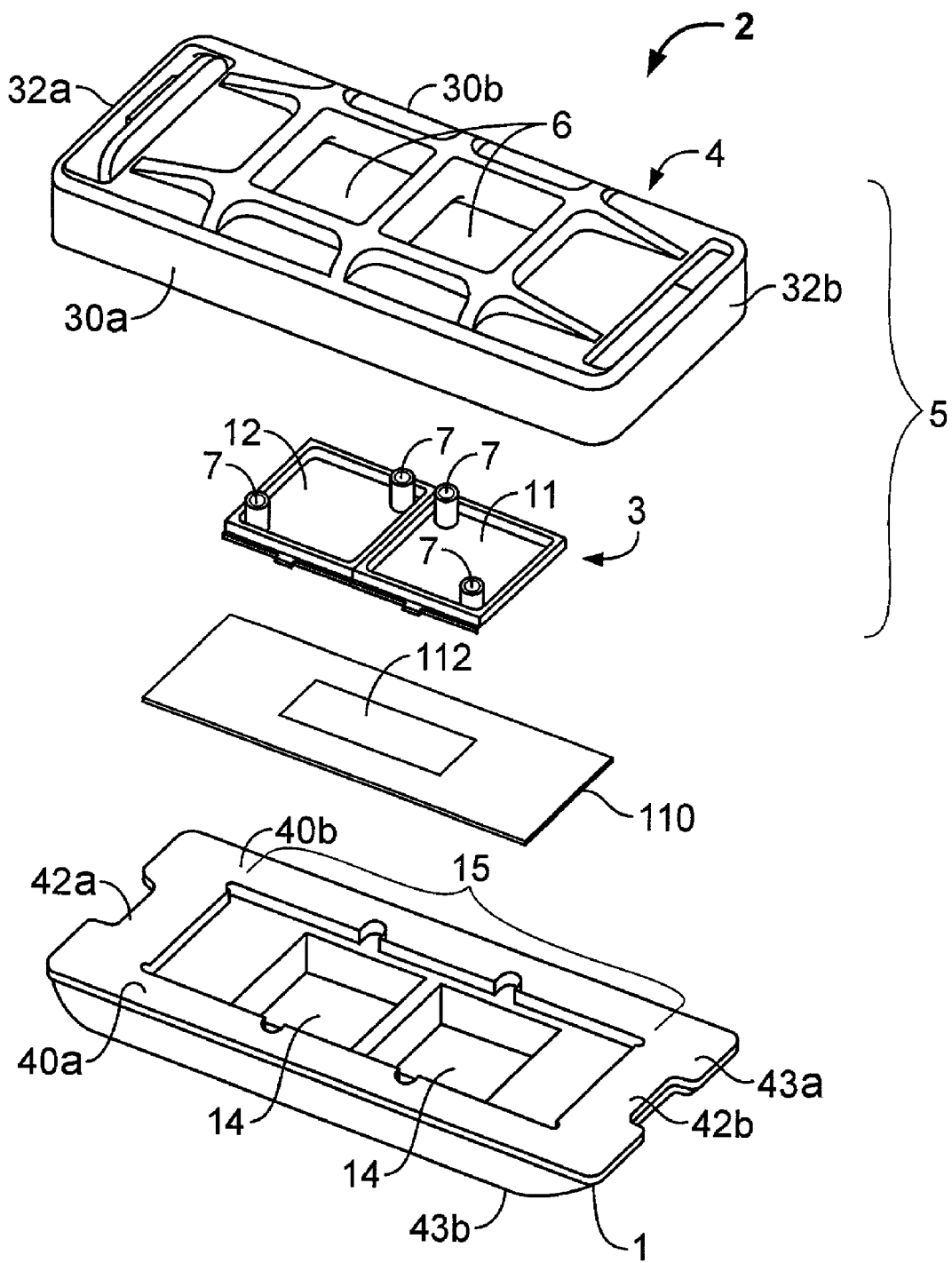
FIG. 4 shows an exploded view of an exemplary embodiment of an array assay device of the present invention.

Turning again to the Figures, an exemplary array assay device 2 of the present invention will now be described in more detail. FIG. 4 shows an exploded view of array assay device 2 shaped to hold substrate 110, herein shown having a rectangular shape, but other shapes may be used as well. Array assay device 2 includes base 1 and cover 5 which are maintained in an assembled, closed configuration using a snap-fit (see FIGS. 7-11). In certain embodiments, the array assay device includes, i.e., is provided with, a substrate having at least one array sealed or assembled in the array assay device. That is, an array assay device is provided to a user with a substrate and array pre-assembled or pre-packaged therein. In this manner, the array assay device serves both as packaging for the substrate and array and as an enclosure during an array assay such that the array assay device and array are ready to use when received by a user such that there is no need for the user to assemble the device and/or insert the substrate and array into the device before use.

The base 1 is dimensioned to hold a substrate carrying at least one array. In this particular embodiment, base 1 has a rectangular shape as mentioned above, with side walls 40*a*, 40*b*, 42*a* and 42*b* and top surface 43*a* and bottom surface 43*b*. The dimensions of the base 1 may vary depending on the size and shape of the substrate to be held by the base 1. By way of example only, where the substrate to be held by the base 1 is a 1" by 3" glass slide, typically, the base 1 has a length that ranges from about 10 mm to about 200 mm, usually from about 20 mm to about 150 mm and more usually from about 22 mm to about 100 mm, the width typically ranges from about 10 mm to about 100 mm, usually from about 20 mm to about 50 mm and more usually from about 22 mm to about 40 mm and the thickness typically ranges from about 4 mm to about 60 mm, usually from about 8 mm to about 40 mm and more usually from about 10 mm to about 30 mm.

The base 1 may also include a substrate receiving area 15, where the substrate to be held by the base 1 may be positioned. For example, the substrate receiving area 15 may be slightly recessed relative to top surface 43*a*, as shown in FIG. 4, having a length, width and thickness closely approximating the corresponding length, width and thickness of a substrate to be held such that the substrate is intimately positioned in the recess. Alternatively, the substrate receiving area 15 may be slightly elevated relative to top surface 43*a* such that a substrate is positioned thereon. The base 1 may be a solid structure or may include one or more openings such as openings 14 which enable a user to visually verify the fluid volume in the array assay device and/or allow the base 1 to be used with an array reader such that the array(s) may be read through the opening(s), as will be described in more detail below. The number of openings 14 present in the base 1 may correspond to the number of arrays present on a substrate held by base 1 or may be a single opening the size of the entire array area, e.g., when the base 1 is used in an array reader. In certain embodiments, the base includes one or more viewing windows, which enable a user to visually verify the fluid volume in the array assay device and/or allow the base 1 to be used with an array reader such that the array(s) may be read through the window(s).

Figure 7:
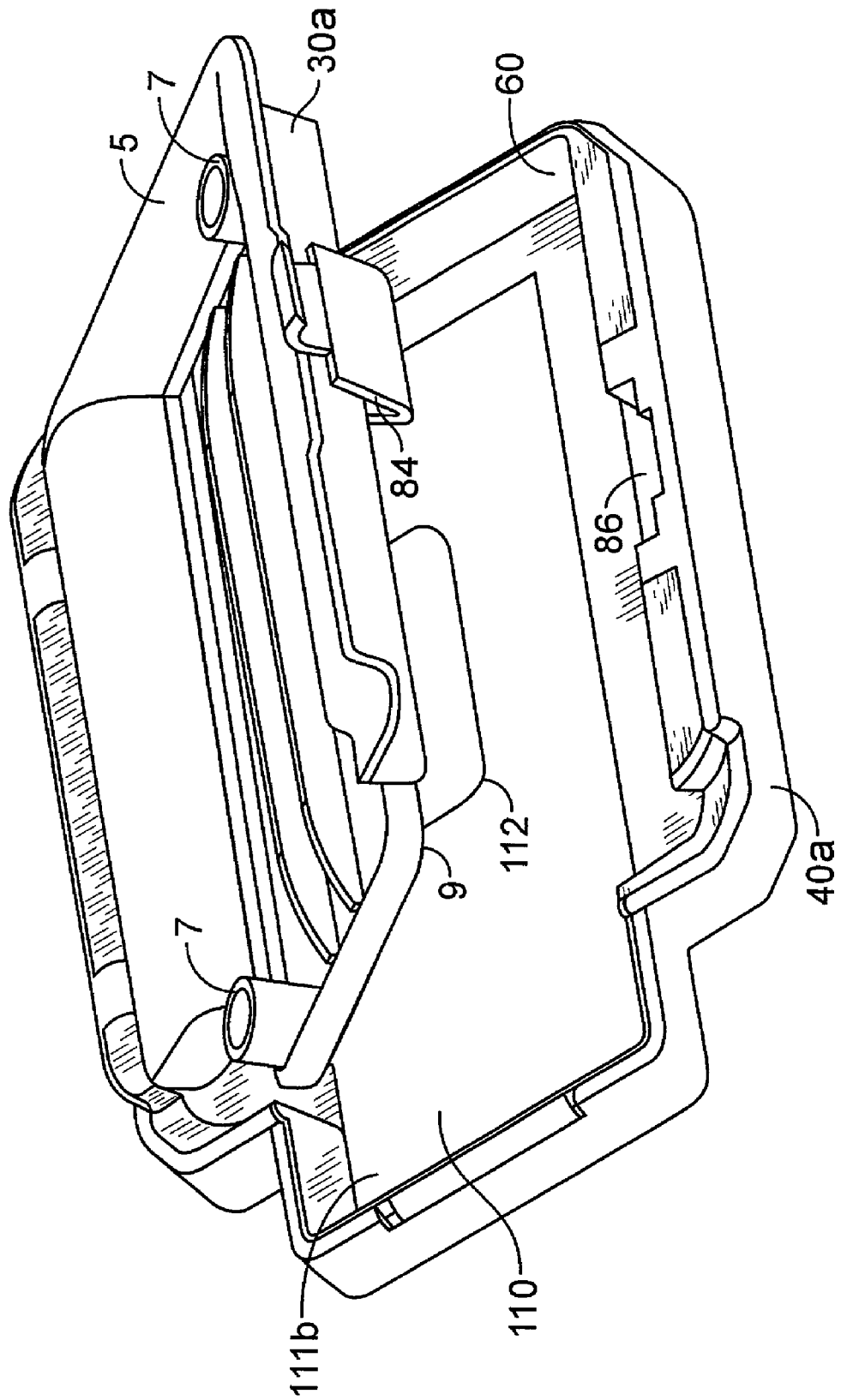
FIG. 7 shows an exemplary embodiment of an array assay device hinged on one side according to the subject invention and having a planar snap-fit.
Figure 15:
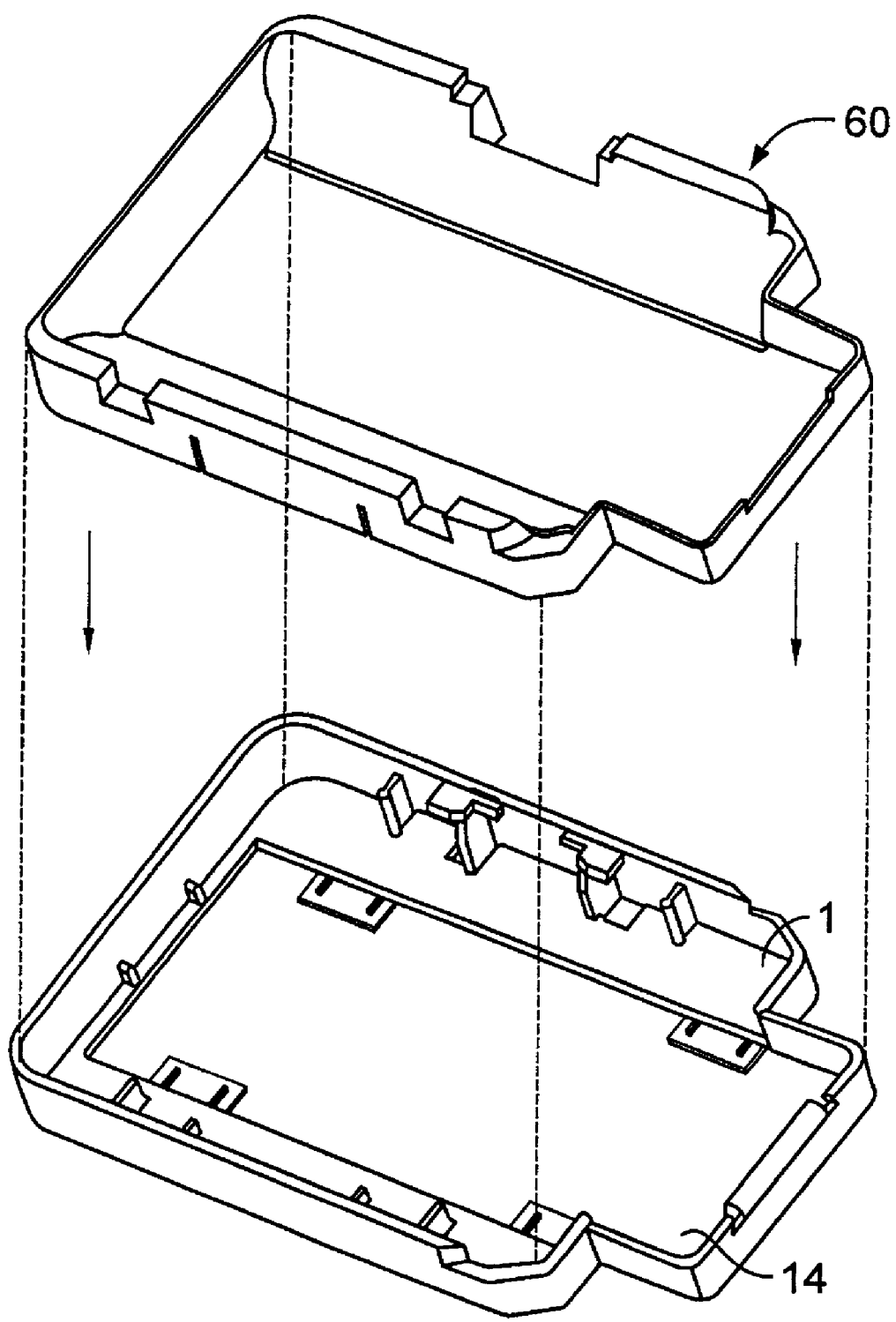
FIG. 15 shows an exemplary embodiment of a subject elastomeric element that is insertable into a subject base.

In certain embodiments of the subject devices, the base 1 includes a deformable elastomeric member 60 positioned therein and upon which the substrate 110 is positioned (see FIG. 7). The deformable elastomeric member 60 is oriented in base 1 such that a lip or ridge of cover 5 will press into it to provide a substantially vapor and fluid tight seal when the base 1 and the cover 5 are snap-fit together. For example, the base 1, or just the inner surface of the base 1, may be coated or lined with an elastomeric material. Alternatively, elastomeric member 60 may be a separate element that is insertable inside the base 1 (see FIG. 15).

Base 1 may be configured to be compatible with an array reader such as a MICROARRAY scanner available from Agilent Technologies of Palo Alto, Calif., such that the base 1, with substrate 110 held thereon, may be directly placed in an array reader so that the array 112 may be read while positioned in the base 1. That is, the base 1 may be used to hold the substrate 110 during the array assay procedure and the reading or scanning of the array. Accordingly, when the base 1 is used to hold the substrate 110 during the reading of array 112, an opening 14 of base 1 will be greater than the dimensions of an array 112 (or of all arrays present) on substrate 110 so the base 1 will not interfere with the reading of the array. A removable plastic shield may be positioned over the opening 14 and/or on surface 111b of substrate 110 to shield the exposed portion of the substrate 110 from damage, fingerprints, marring, and the like.

Figure 5:
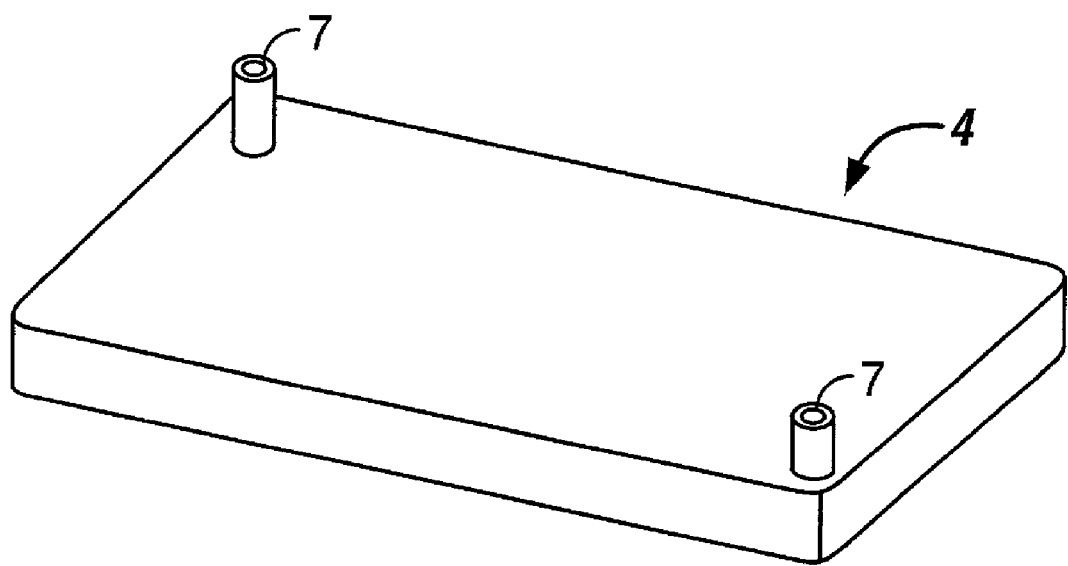
FIG. 5 shows a plan view of a cover having an assay area element and a housing that are integrally formed.

The cover 5 of the array assay device 2 is shaped and dimensioned to cover the substrate 110 held by the base 1 when the base 1 and the cover 5 are snap-fit together. As mentioned above, when snap-fit together, the base 1 and the cover 5 enclose a space between the base 1 and the cover 5. Accordingly, cover 5 (and in certain embodiments base 1) includes at least one recess configured to provide this enclosed space. FIG. 4 shows cover 5 made of two components: an assay area element 3 having at least one recess 9 and a housing 4, however, it will be apparent that the assay area element 3 may be formed or molded integral to the housing 4 as one piece, such as shown in FIGS. 5 and 7. That is, the cover 5 may be a unitary piece of construction or rather a single element. For ease of description only, the cover 5 will be described herein as two separate components: an assay area element 3 and a housing 4.

In the embodiments shown herein, the housing 4 has a rectangular shape corresponding to the shape of base 1, and thus has side walls 30a, 30b and 32a and 32b. The dimensions of the housing 4 may vary depending on the size and shape of the base 1, the size and shape of the substrate to be enclosed by the array assay device 2, etc. By way of example only, where the array substrate to be held by the base 1 is a 1" by 3" glass slide, typically, the housing 4 has a length that ranges from about 10 mm to about 200 mm, usually from about 20 mm to about 150 mm and more usually from about 22 mm to about 100 mm, the width typically ranges from about 10 mm to about 100 mm, usually from about 20 mm to about 50 mm and more usually from about 22 mm to about 40 mm and the thickness typically ranges from about 4 mm to about 60 mm, usually from about 8 mm to about 40 mm and more usually from about 10 mm to about 30 mm. If an assay area element 3 is employed, the housing 4 will include at least one opening 6 dimensioned so that one or more access ports 7 positioned on assay area element 3 may protrude therethrough so they may be accessible from a location outside the array assay device 2.

Assay area element 3 is dimensioned to be positioned over a substrate 10 that has been positioned on the base 1 so that the assay area element 3 covers the substrate 110. More specifically, the assay area element 3 is dimensioned to cover the substrate 110 and provide an area or space over at least one array on the substrate, where such an area defines an assay area. Accordingly, the assay area element 3 may assume a variety of shapes, so long as a space or assay area having a volume from about 10 µl to about 1000 µl is able to be enclosed around at least one array on the substrate 110 when the base 1 and the cover 5 are snap-fit together. For example, the substrate 110 may be round and the assay area element 3 may also be round, etc. FIG. 4 shows assay area element 3 which includes two sections 11 and 12, corresponding to two arrays on substrate 110, however, greater or fewer sections may be used, depending on the number of arrays 112 on substrate 110. In the case where two sections are provided, two assay areas are defined thereby when operatively contacted with a substrate. Typically, as shown in FIG. 4, each section 11 and 12 has a least one access port 7 for the introduction and/or removal of fluid and/or gases from the array assay device 2. To minimize fluid loss through the ports 7, the access ports 7 may also include a closure element (not shown) such as duckbill valves, caps, check valves, self-sealing gaskets, and the like. It will be appreciated that any number of access ports 7 may be used, herein shown as two access ports 7 per section, but greater or fewer access ports 7 may be employed.

Figure 6:
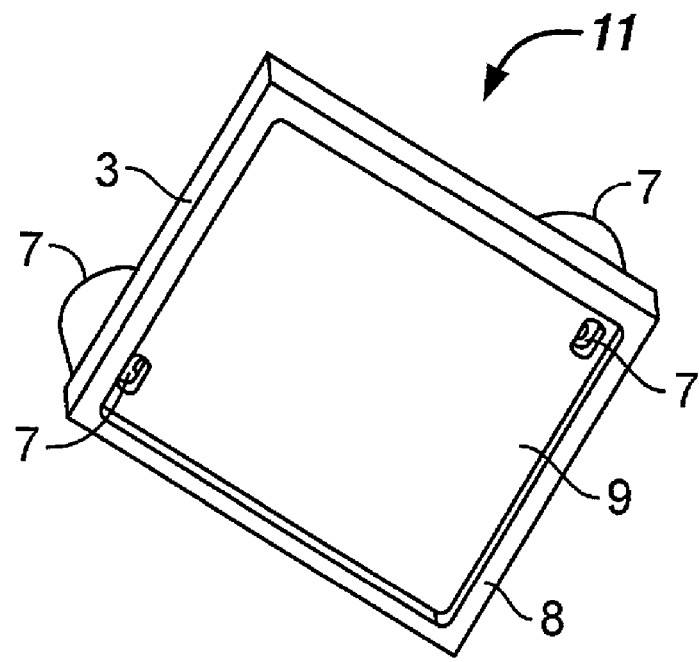
FIG. 6 shows a perspective view of the underside of the cover shown in FIG. 4.

FIG. 6 shows the inner surface of assay area element 3, herein described with reference to section 11 for ease of description only. Section 11 of assay area element 3 has a recessed portion 9 such that when the base 1 and the cover 5 are snap-fit together, the assay area element 3 is positioned over the substrate 110, over an array 112, to provide an assay area, as mentioned above, defined by the enclosed area or space between the substrate 10 and the recess 9. Accordingly, the assay area produced is substantially vapor and fluid tight due to the substantially vapor and fluid tight seal formed between the perimeter, i.e., the walls or edges of recess 9 and the substrate 10. More specifically, when engaged, the snap-fit applies a pressure to the outer surface of the assay area element 3 directly above the recess 9 and more specifically to the perimeter of recess 9 to produce a substantially vapor and fluid tight seal with a substrate positioned on the base 1.

The volume of the enclosed space, i.e., the assay area volume, associated with each array may vary depending on the specific array substrate size, the number of arrays, the type of array assay performed, etc. In many embodiments of the subject array assay devices, the volume of the assay area ranges from about 10 µl to about 1000 µl. It is apparent that in the embodiment in FIG. 4, two assay areas are formed by snap-fitting the cover and the base together, which positions the two sections 11 and 12 of assay area element 3 over two arrays on the substrate 110 held by base 1. In other embodiments, substrate 110 has one array and the assay area element 3 will then have one section or one single recess 9, so only one assay area is formed. Alternatively, the substrate 110 may have more than two arrays and the assay area element 3 may have a corresponding number of sections so that an individual assay area is provided around each, and typically only one, array to provide respective assay areas. In still other embodiments, more than one assay area element may be used, i.e., the sections are not contiguous, but rather are two separate sections. The sections of assay area element 3 may be configured to be easily connected or joined to other sections, e.g., by a user, to accommodate any number of arrays present on a substrate.

The subject array assay devices also include a sealing element 8 which forms a seal around the array(s) on the substrate. By sealing element is meant any sealing device or structure that produces a seal between two surfaces, such as a gasket, a lip, ledge or ridge, material interface, viscous sealant, or the like and which does not substantially adversely interfere with the array assay such as by leaching, nonspecific binding, or other physical or chemical degradation. FIG. 5 shows sealing element 8 configured as a lip positioned around the perimeter of recess 9 of assay area element 3. In this embodiment, lip 8 includes an elastomeric material, e.g., made entirely of or coated with, which forms a substantially vapor and fluid tight seal when pressed against the substrate 110 to form an assay area. However, other sealing elements are possible as well. For example, the sealing element 8 may be a separate component positioned between the substrate 110 and cover 5 or may be positioned on the substrate 110.

FIG. 7 shows another exemplary embodiment of the subject array assay devices having the base 1 and the cover 5 secured together on one side, for example by a hinge, and having an elastomeric material 60 positioned in base 1, as described above.

As mentioned above, a feature of the subject invention is that the components of the subject array assay devices are configured to be snap-fit together or joined by a snap-fit feature or snap-fit attachment. By snap-fit is meant any suitable "built in" or integral latching or attachment feature or mechanism for attaching one part or element to another, such as for attaching the base to the cover of the subject invention. A snap-fit attachment does not require any additional pieces, materials or tools to carry out the function of attachment. Representative snap-fits suitable for use with the present invention are described in Bonenberger, P., The First Snap-Fit Handbook, Hanzer (2000), incorporated herein in its entirety. That is, the subject devices are not assembled or held together with screws, clamps or the like and instead are easily assembled by simply snapping the base and the cover together using a snap-fit and easily disassembled by disengaging or unsnapping the snap-fit. The subject devices are also easily disassembled by disengaging or un-snapping the snap-fit. When the cover 5 is snap-fit to the base 1, the snap-fit, a pressure or force is applied to the seal between the recess 9 and the substrate 110 to improve the seal, as mentioned above.

Any convenient snap-fit may be used to operatively hold the base 1 and the cover 5 together in a closed configuration, where the particular snap-fit used will be chosen with respect to a variety of factors such as the shape of the array assay device, the materials of the array assay device, etc. Snap-fits may be releasable or nonreleasable, but typically will be releasable. Representative snap-fits suitable for use with the subject invention include, but are not limited to, a planar snap-fit, a cantilever snap-fit, a torsion snap-fit and an annular snap-fit, where more than one of the same or different type of snap-fit may be used. Representative snap-fits suitable for use in the subject invention will now be described in more detail, where such snap-fits, and analogous snap-fits, are well known to those of skill in the art. It will be understood that the one or more snap-fits employed may be positioned in any convenient location on or in a subject device, i.e., in or on any suitable surface, wall, edge, etc., of the subject device, where the positioning shown in the Figures is for exemplary purposes only and is in no way intended to limit the scope of the invention.

Planar Snap-Fit

As mentioned above, a planar snap-fit may be used to hold the base and the cover of the subject device engaged together in a closed configuration. Generally, a planar snap-fit includes a catch positioned on one surface such as a surface of the base and a mateable recess or hole positioned on a corresponding surface such as a surface of the cover.

FIG. 8 shows an exemplary embodiment of a planar snap-fit having a catch 70 positioned on a surface of base 1 and a mateable recess 72 operatively positioned on a surface of a cover 5 to restrain the catch 70.

Torsion Snap-Fit

A torsion snap-fit may also be used to hold the base 1 and the cover 5 together. Torsional snap-fits primarily use torsional deflection for assembly. Generally, torsion snap-fits include a spring loaded lever. In use, the spring-loaded lever snaps into place when the mating part is pressed into place. Exemplary torsional snap-fits are shown in FIGS. 9A, 9B, 9C, 9D and 9E. FIG. 9A shows an exemplary embodiment of torsional snap fit attachment 90 (mateable portion not shown). FIG. 9B shows an exemplary embodiment of torsional snap fit attachment 92 (mateable portion not shown). FIG. 9C shows an exemplary embodiment of torsional snap fit attachment 94 (mateable portion not shown). FIG. 9D shows an exemplary embodiment of torsional snap fit attachment 96 (mateable portion not shown). FIG. 9E shows an exemplary embodiment of torsional snap fit attachment 97.

Annular Snap-Fit

An annular snap-fit may also be used to hold the base 1 and the cover 5 together. Generally, an annular snap-fit, similar to the snap-fits used with snap-on caps on ball point pens, involve the interference between concentric ridges and rely of radial elasticity for assembly and retention. FIGS. 10A and 10B show exemplary embodiments of annular snap-fits suitable for use with the subject invention.

Cantilever Snap-Fit

A cantilever snap-fit may be used with the subject invention. In general, a cantilever snap-fit includes a cantilever lock made up of a beam or protrusion and a corresponding mating constraint feature. Cantilever shaped snaps may assume a variety of shapes such as a cantilever beam snap-fit design, as well as other designs such as "L" and "U" shaped cantilevers. FIG. 11A shows a typical cantilever lock 80 positioned on a surface of base 1 and a corresponding constraint feature 82 operatively positioned on a surface of a cover 5. FIG. 11B shows another embodiment of a cantilever lock 84 positioned on a surface of a cover 5. "L" shaped cantilever lock 84 is also shown in FIG. 7 with corresponding mating constraint feature 86 operatively positioned on base 1. FIG. 11C shows another exemplary cantilever lock 88 and corresponding restraint feature 89. FIG. 11D shows an exemplary "U" shaped cantilever 85.

Substrate Receiving Frame

Also provided by the subject invention are substrate receiving frames for positioning a substrate 110 having at least one array 112 therein before being positioned on base 1. The subject substrate receiving frames serve multiple purposes such as substrate edge protection, compatibility with array scanners and the ability to grasp and manipulate a substrate 110 without contacting the array 112 thereon, e.g., during a wash protocol, during transport, e.g., to an array reader, and the like.

Figure 12:
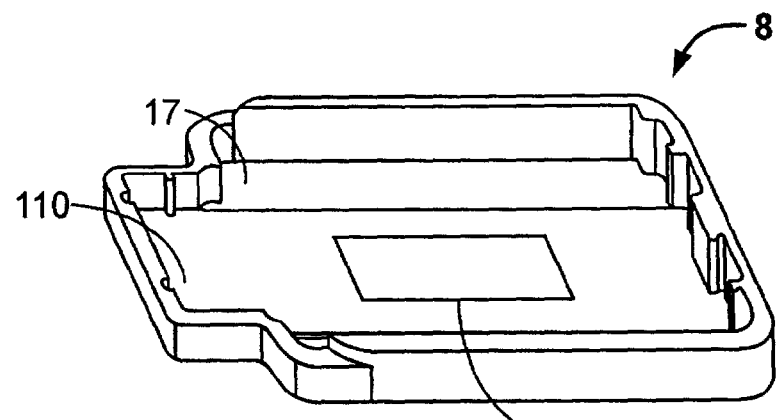
FIG. 12 shows an exemplary embodiment of a substrate receiving frame according to the subject invention.

FIG. 12 shows an exemplary embodiment of a substrate receiving frame 8 having substrate 110 positioned therein. Substrate receiving frame 8 has an opening 17 for positioning the substrate 110 therein using any suitable mechanical, physical or chemical means. Usually, the frame 8 will include ledges or pegs or rails (not shown) onto which the substrate 110 is positioned. The substrate receiving frame 8 may be compatible with an array reader such as a MICROARRAY scanner available from Agilent Technologies of Palo Alto, Calif. where such a compatible array reader will typically have a suitable mounting means for receiving and releasably retaining the substrate receiving frame 8 in a known position. Accordingly, after the array assay is complete, the snap-fit may be disengaged and the cover 5 separated from the base 1. The frame 8 with the substrate 10 therein may be removed from the array assay device 2 and may then be directly placed into an array reader. That is, the substrate receiving frame 8 may be used as a means to hold a substrate 110 both during the assay and the reading of the array.

The size and shape of a substrate receiving frame 8 may vary according to the size and shape of the substrate 110 and corresponding array assay device. By way of example only and not limitation, in certain embodiments the substrate receiving frame 8 is rectangular in shape and the length thereof typically ranges from about 10 mm to about 200 mm, usually from about 20 mm to about 150 mm and more usually from about 22 mm to about 100 mm, the width typically ranges from about 10 mm to about 100 mm, usually from about 20 mm to about 50 mm and more usually from about 22 mm to about 40 mm and the thickness typically ranges from about 4 mm to about 60 mm, usually from about 8 mm to about 40 mm and more usually from about 10 mm to about 30 mm.

Furthermore, the subject substrate receiving frames 8 may be manufactured from a variety of materials, with the only limitation being that the such materials used to fabricate the subject frames will not substantially interfere with the assay reagents and the assay and will have minimal non specific binding characteristics, e.g., substantially chemically inert, thermally stable, etc. Specifically, the materials should be chemically and physically stable under conditions employed for array assay procedures. Examples of such materials may include, but are not limited to, plastics such as polytetrafluoroethylene, polypropylene, polystyrene, polycarbonate, PVC, and blends thereof, elastomers, stainless steel and alloys thereof, siliceous materials, e.g., glasses, fused silica, ceramics and the like. In those embodiments where the substrate receiving frame 8 is also compatible and thus used with an array reader or scanner, the material used will be compatible with the reader as well. For example, where the reader is an optical scanner, the material of the substrate receiving frame 8 will usually be opaque, such as an opaque plastic, e.g., black acrylonitrile-butadiene-styrene (ABS) plastic (although other material could be used as well).

Array Holders

Also provided by the subject invention are array holders suitable for use with the subject hybridization chambers. More specifically, the subject array holders are used to retain the substrates which include one or more arrays. The array holders of the subject invention are configured to be inserted into the subject array assay devices and may also be configured to be compatible with array scanners or readers for interrogating or reading the array after an assay has been performed such as a hybridization assay or the like, e.g., array optical scanners such as the MICROARRAY scanner available from Agilent Technologies, Inc. of Palo Alto, Calif., where such a compatible scanner will typically have a suitable mounting means for receiving and releasably retaining the holder in a known position.

The subject array holders serve multiple purposes such as substrate edge protection, compatibility with array scanners and the ability to grasp and manipulate an array without contacting the array itself, e.g., during a wash protocol, during transport, e.g., to an array reader, and the like.

Furthermore, the array holders enable a wide range of substrate sizes to be used with the subject array hybridization chambers. That is, a substrate shorter in length than a typical substrate such as a typical 1" by 3" microscope slide, may be first retained in the array holder which itself is about 1" by about 3", or is the size of a typical substrate or of a suitable size that is compatible with the array assay device. Thus, when a substrate having a length shorter than about 3" is retained by a holder, the shorter substrate may still be used with a subject array assay device. In certain embodiments, spacers may be added to the holder as well to accommodate the remaining volume/area remaining from the shorter length substrate to allow an appropriate seal to be formed therewith and the volume within the assay area(s) to remain constant no matter the dimensions of the substrate.

Figure 13:
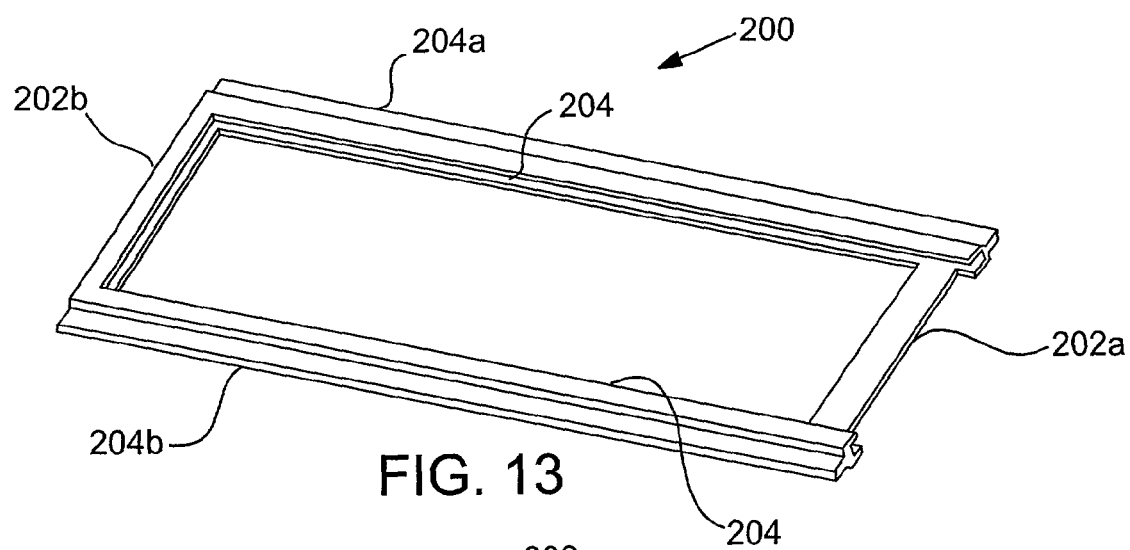
FIG. 13 shows an exemplary embodiment of an array holder according to the subject invention.
Figure 14:
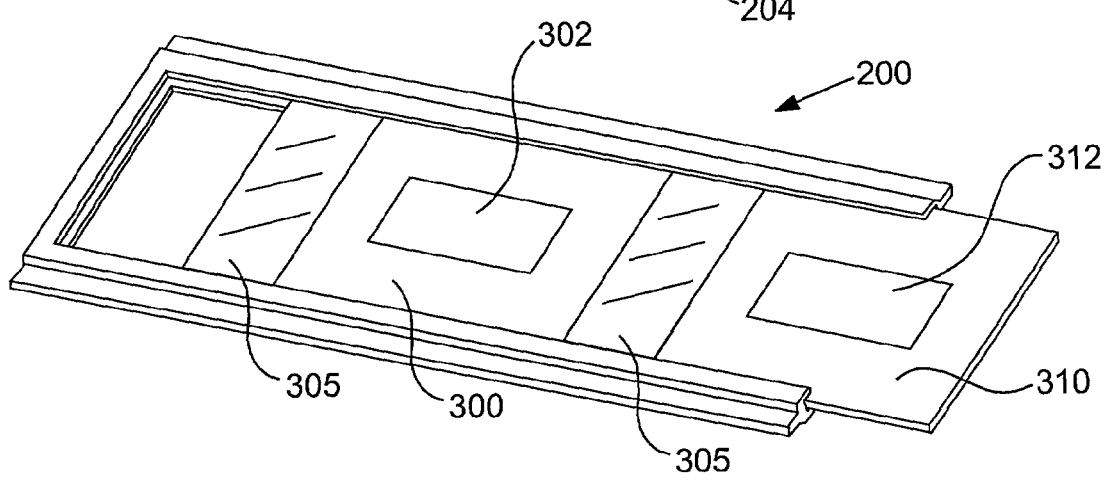
FIG. 14 shows the array holder of FIG. 13 having reduced length substrates with at least one array thereon inserted therein.

FIG. 13 shows an exemplary embodiment of a subject array holder. Array holder 200 includes two opposed side portions 204a and 204b with a channel 206 positioned therebetween, and extending in a direction between open end 202a and closed end 202b. Opposed side portions 204a and 204b have ledges 204 running the lengths of side portions 204a and 204b which receive and retain a substrate, i.e. upon which a substrate rests. In use, a substrate is inserted into holder 200 via open end 202a. FIG. 14 shows holder 200 having a substrate 300 retained therein and a substrate 310 partially inserted through open end 202a. As is shown, substrates 300 and 310 have lengths shorter than the length of the holder 200 and thus spacers 305 are used to take-up the remaining space.

The size and shape of an array holder may vary according to the size and shape of a substrate and corresponding array assay device. By way of example only and not limitation, in certain embodiments the array holder is rectangular in shape and the length thereof typically ranges from about 10 mm to about 200 mm, usually from about 20 mm to about 150 mm and more usually from about 22 mm to about 100 mm, the width typically ranges from about 10 mm to about 100 mm, usually from about 20 mm to about 50 mm and more usually from about 22 mm to about 40 mm and the thickness typically ranges from about 4 mm to about 60 mm, usually from about 8 mm to about 40 mm and more usually from about 10 mm to about 30 mm.

Furthermore, the subject holders may be manufactured from a variety of materials, with the only limitation being that the such materials used to fabricate the subject holders will not substantially interfere with the assay reagents, the assay and will have minimal non specific binding characteristics, e.g., substantially chemically inert, thermally stable, etc. Specifically, the materials should be chemically and physically stable under conditions employed for array assay procedures. Examples of such materials may include, but are not limited to, plastics such as polytetrafluoroethylene, polypropylene, polystyrene, polycarbonate, PVC, and blends thereof, elastomers, stainless steel and alloys thereof, siliceous materials, e.g., glasses, fused silica, ceramics and the like. In those embodiments where the array holder is also compatible and thus used with an array reader or scanner, the material used will be compatible with the reader as well For example, where the reader is an optical scanner, the material of the array holder will usually be opaque, such as an opaque plastic, e.g., black acrylonitrile-butadiene-styrene (ABS) plastic (although other material could be used as well).

Methods of Using Array Assay Devices

As summarized above, methods are also provided for performing an array based assay such as a hybridization assay or any other analogous binding interaction assay.

Generally, a sample suspected of including an analyte of interest, i.e., a target molecule, is contacted with an array mounted in a subject array assay device under conditions sufficient for the analyte target in the sample to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system, e.g., an isotopic or fluorescent label present on the analyte, etc., as described above. The presence of the analyte in the sample is then deduced from the detection of binding complexes on the substrate surface.

As mentioned above, the subject methods may be used in a variety of array based assays, where hybridization reactions will be used herein for exemplary purposes only, and is not intended to limit the scope of the invention. In hybridization assays, a sample of target analyte such as target nucleic acids is first prepared, where preparation may include labeling of the target nucleic acids with a label, e.g., with a member of signal producing system and the sample is then contacted with the array under stringent hybridization conditions, whereby complexes or duplexes are formed between target analytes such as nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patent applications describing methods of using arrays in various applications include: WO 95/21265; WO 96/31622; WO 97/10365; WO 97/27317; EP 373 203; and EP 785 280 and U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of the U.S. patents which are herein incorporated by reference.

In practicing the subject methods, the first step is to provide a subject array assay device 2, as described above. After the provision of a subject array assay device 2 is met, a substrate 110 having at least one array 112 is operatively positioned on the base 1. In certain embodiments of the subject invention, the substrate 110 is first positioned in a substrate receiving frame 8 and/or an array holder 200 before being positioned on the base 1. In certain embodiments, the base 1 includes an elastomeric material, upon which the substrate 110 is positioned or which surrounds the substrate 110 when the substrate 110 is positioned in the base 1 (see for example FIGS. 7 and 15). In all embodiments of the subject invention, the substrate 110 is positioned on the base 1 such that the array side 111b faces the cover 5. In those embodiments employing a base 1 having an opening 14 therein, a removable protective shield, as described above, is usually positioned over the opening 14 and/or the non array surface 111a of the substrate 110 so as to protect the substrate 110 from damage, fingerprints, marring, etc.

Next, the base 1 and the cover 5 are joined together in a closed configuration and retained in the closed configuration by snap-fit to enclose a space or area between the base 1 and the cover 5. Any convenient snap-fit may be used, as described above, including, but not limited to, a planar snap-fit, a cantilever snap-fit, a torsion snap-fit and an annular snap-fit. The snap-fit may be releasable or nonreleasable, but will typically be releasable. By engaging the snap-fit, a space or area is enclose between the base 1 and the cover 5 defined by the recess 9 in the cover 5 and the substrate 110 and pressure is applied to the perimeter or substrate contacting edges of recess 9 to produce a substantially vapor and fluid tight seal. That is, a space or area is produced by providing a seal around at least one array 112 with a substantially vapor and fluid tight seal to produce a substantially vapor and fluid tight assay area around the sealed array 112. The space or assay area that is enclosed has a volume around each array, i.e., an assay volume, that usually ranges from about 10 µl to about 1000 µl. If a plurality of arrays 112 is present on substrate 110, usually a substantially vapor and fluid tight seal is produced around each array so as to provide individual vapor tight assay areas around each array.

As mentioned above, the substrate having at least on array may be provided to the user pre-assembled or pre-packaged in the interior of the array assay device 2. For example, the array assay device may serve as the packaging for the substrate and array during transport from a remote manufacturer to the user, where an array assay is then performed in the same array assay device as that which is used as packaging for the substrate and at least one array.

Once one or more substantially vapor and fluid tight seals produce one or more assay areas around one or more arrays, the array 112 is contacted with a fluid sample suspected of containing target analyte, e.g., target nucleic acids, that are complementary to probe sequences attached to the array surface. As will be apparent to those of skill in the art, the sample may be any suitable sample which includes a member of a specific binding pair. That is, the sample will be a sample capable of binding with a biopolymeric probe bound to the surface of the substrate. Typically, the sample includes the target analyte, often pre-amplified and labeled.

Thus, at some prior to the detection step, described below, any target analyte present in the initial sample contacted with the array 112 is labeled with a detectable label. Labeling can occur either prior to or following contact with the array. In other words, the analyte, e.g., nucleic acids, present in the fluid sample contacted with the array may be labeled prior to or after contact, e.g., hybridization, with the array. In some embodiments of the subject methods, the sample analytes e.g., nucleic acids are directly labeled with a detectable label, wherein the label may be covalently or non-covalently attached to the nucleic acids of the sample. For example, the nucleic acids, including the target nucleotide sequence, may be labeled with biotin, exposed to hybridization conditions, wherein the labeled target nucleotide sequence binds to an avidin-label or an avidin-generating species. In an alternative embodiment, the target analyte such as the target nucleotide sequence is indirectly labeled with a detectable label, wherein the label may be covalently or non-covalently attached to the target nucleotide sequence. For example, the label may be non-covalently attached to a linker group, which in turn is (i) covalently attached to the target nucleotide sequence, or (ii) comprises a sequence which is complementary to the target nucleotide sequence. In another example, the probes may be extended, after hybridization, using chain-extension technology or sandwich-assay technology to generate a detectable signal (see, e.g., U.S. Pat. No. 5,200,314, the disclosure of which is herein incorporated by reference). Generally, such detectable labels include, but are not limited to, radioactive isotopes, fluorescers, chemiluminescers, enzymes, enzyme substrates, enzyme cofactors, enzyme inhibitors, dyes, metal ions, metal sols, ligands (e.g., biotin or haptens) and the like.

In one embodiment, the label is a fluorescent compound, i.e., capable of emitting radiation (visible or invisible) upon stimulation by radiation of a wavelength different from that of the emitted radiation, or through other manners of excitation, e.g. chemical or non-radiative energy transfer. The label may be a fluorescent dye. Usually, a target with a fluorescent label includes a fluorescent group covalently attached to a nucleic acid molecule capable of binding specifically to the complementary probe nucleotide sequence.

Accordingly, sample is introduced into the array assay device 2 and more specifically to the sealed assay area(s) formed around the one or more arrays 112, where the sample is retained therein due to the vapor and fluid tight seal of the assay area so that the array 112 does not dry out. The sample is thus introduced into one or more assay areas via one or more access ports 7 either manually or automatically. Thus, each assay area may be accessible through at least one port 7 and sample may be introduced into respective assay areas through respective assay ports, e.g., introduced through one respective port and vented through another port. That is, the sample may be introduced using a pipette, syringe or any other suitable introduction means. In certain embodiments, one port provides a vent and sample is introduced through another port. Once introduced into an assay area, the sample is substantially confined to the assay area. In this regard, multiple samples may be tested with multiple arrays without cross contamination, i.e., multiple samples may be introduced into different assay areas, where the samples may be the same or different.

The subject invention also includes methods for mixing fluid in an assay area, e.g., sample and/or wash fluid, where the fluid may be mixed using any convenient method such as shaking, rotation, etc. In one embodiment, described in detail in U.S. Pat. No. 6,258,593, the disclosure of which is incorporated by reference, a bubble is provided in the assay area by incomplete filling of the assay area or by addition of a gas to the assay area with the fluid, where the assay area may further include a surfactant to facilitate the mixing. Mixing is accomplished by moving the bubble within the assay area during the reaction to displace the fluid therein.

Accordingly, the sample is contacted with the array under stringent conditions to form binding complexes on the surface of the substrate by the interaction of the surface-bound probe molecule and the complementary target molecule in the sample. In the case of hybridization assays, the sample is contacted with the array under stringent hybridization conditions, whereby complexes are formed between target nucleic acids that are complementary to probe sequences attached to the array surface, i.e., duplex nucleic acids are formed on the surface of the substrate by the interaction of the probe nucleic acid and its complement target nucleic acid present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, followed by washing the filters in 0.1×SCC at about 65° C. Hybridization involving nucleic acids generally takes from about 30 minutes to about 24 hours, but may vary as required. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Once the incubation step is complete, the array 112 is washed at least one time to remove any unbound and non-specifically bound sample from the substrate 110, generally at least two wash cycles are used. Washing agents used in array assays are known in the art and, of course, may vary depending on the particular binding pair used in the particular assay. For example, in those embodiments employing nucleic acid hybridization, washing agents of interest include, but are not limited to, salt solutions such as sodium, sodium phosphate and sodium, sodium chloride and the like as is known in the art, at different concentrations and may include some surfactant as well.

In washing the substrate 110 and more specifically the at least one array 112 thereon, the substrate 110 may be removed from the array assay device 2 or may be washed while still positioned in the device 2. To remove the substrate 110 from the array assay device 2, the user disengages or un-snaps the snap-fit attachment and separates the base 1 from the cover 5, i.e., opens the device. If the substrate 110 is removed from the array assay device 2 for washing, the substrate 110 may remain in the substrate receiving frame 8 and/or the array holder 200, if used, during washing so that the user may simply engage the substrate receiving frame 8 and/or the array holder 200 during washing and not the substrate 110 itself, thereby minimizing contamination of the array 112. Similarly, the substrate 110 may remain in the base 1, for example if the base 1 is configured to be used with an array scanner. Typically, the protective shield is removed from the substrate 110, if previously attached thereto. In those embodiments where the substrate 110 remains in the array assay device 2 during washing, fluid may be removed through an access port 7 and wash fluid may be introduced through an access port 7.

Following the washing procedure, as described above, the at least one array 112 is then interrogated or read so that the presence of the binding complexes is then detected i.e., the label is detected using colorimetric, fluorimetric, chemiluminescent or bioluminescent means. If not already done, e.g., for the washing steps, the substrate 110 is removed from the array assay device 2 for reading by disengaging or un-snapping the snap-fit, as described above. The substrate 110 may remain positioned on the base 1, if the base 1 is to be used in the array reader (where the protective shield is removed prior to reading), and/or may remain positioned in the substrate receiving frame 8 and/or array holder 200, if used, if the substrate receiving frame 8 and/or the array holder 200 is to be used in the array reader.

Accordingly, the subject methods also include retaining a substrate 110 having at least one array 112 in a substrate receiving frame 8 and/or an array holder 200, positioning the at least one array retained in the frame and/or holder in an array assay device and performing an array assay with the at least one array in the frame and/or holder. Following the completion of the array assay, the frame and/or the holder with the substrate 110 having at least one array 112 retained thereby is removed from the array assay device and directly placed, i.e., operatively mounted, into or on an array scanner or reader. In this manner, the at least one array may then be read or scanned by the array reader while the array is still held by the substrate receiving frame and/or array holder. That is, the substrate receiving frame and/or array holder may be used to handle a substrate 110 having at least one array both during the assay and during the scanning or reading of the array. The above described general methods for positioning and retaining a substrate having at least one array in a substrate receiving frame and/or an array holder, placing the retained substrate having at least one array in an array assay device, performing an array assay using the array assay device and retained substrate, removing the retained substrate having at least one array from the array assay device and mounting the retained substrate, i.e., the substrate held by the receiving frame and/or array holder, in or on an array scanner and scanning the at least one array while the array is retained by the substrate receiving frame and/or the array holder may be employed with the array assay devices described herein or any analogous array assay device. For example, the above described methods may be employed using the array assay devices described in copending U.S. application Ser. No. 10/177,376, entitled "Array Assay Devices and Methods of Using the Same", to Shea, et at, filed on even date herewith; copending U.S. application Ser. No. 10/179,939, entitled "Array Assay Devices and Methods of Using the Same", to Shea, et al., filed on even date herewith; and copending U.S. application Ser. No. 10/179,938, entitled "Array Assay Devices and Methods of Using the Same", to Shea, et al., filed on even date herewith, the disclosures of which are herein incorporated by reference.

Reading of the at least one array 112 may be accomplished by illuminating the at least one array 112 and reading the location and intensity of resulting fluorescence at each feature of the array to obtain a result. For example, a scanner may be used for this purpose which is similar to the MICROARRAY scanner available from Agilent Technologies, Palo Alto, Calif. Other suitable apparatus and methods for reading an array are described in U.S. patent application Ser. No. Ser. No. 20/087,447 "Reading Dry Chemical Arrays Through The Substrate" by Dorsal et al., Ser. No. 09/846,125 "Reading Multi-Featured Arrays" by Dorsel et al.; and Ser. No. 09/430,214 "Interrogating Multi-Featured Arrays" by Dorsel et al., the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,251,685; 6,221,583, the disclosure of which is herein incorporated by reference, and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array 112 (such as whether or not a particular target sequence may have been present in the sample or whether or not a pattern indicates a particular condition of an organism from which the sample came). The results of the reading (whether further processed or not) may be forwarded (such as by communication) to a remote location if desired, and received there for further use (such as further processing).

The subject methods may also include pre-assembling or pre-packaging, i.e., pre-loading, a substrate having at least one array in an array assay device at a first site, e.g., a manufacturing facility or the like, and transporting the pre-packaged substrate to a second site for use in an array assay. By "second site" in this context is meant a site other than the site at which the array is pre-packaged in the array assay device. For example, a second site could be another site (e.g., another office, lab, etc.) in the same building, city, another location in a different city, another location in a different state, another location in a different country, etc. Usually, though not always, the first site and the second site are at least in different buildings, and may be at least one mile, ten miles, or at least one hundred miles apart. "Transporting" in this context refers to any means of getting the pre-packaged array(s) from one site to the next, i.e., physically moving or shipping the pre-packaged array(s) to a second site. Once the array assay device with the substrate having at least one array pre-assembled or pre-packaged therein is received by a user at the second site, an array assay is performed using the array assay device and pre-packaged array(s). Following completion of the array assay, the substrate having at least one array is removed from the array assay device, positioned on an array scanner or reader and the at least one array is scanned by the array reader to obtain a result, as described above. As mentioned above, the substrate may be positioned in a substrate receiving frame and/or array holder prior to placement in an array assay device and the substrate may be retained in the substrate receiving frame and/or array holder during the scanning or reading of the at least one array, i.e., the substrate receiving frame and/or array holder may be operatively mounted on a scanner so that the array(s) may be scanned or read while retained in the substrate receiving frame and/or array holder to obtain a result. The above described general methods of array use may be employed with the array assay devices described herein or any analogous array assay device, for example those described in copending U.S. application Ser. No. 10/177,376, entitled "Array Assay Devices and Methods of Using the Same", to Shea, et al., filed on even date herewith; copending U.S. application Ser. No. 10/179,939, entitled "Array Assay Devices and Methods of Using the Same", to Shea, et al., filed on even date herewith; and copending U.S. application Ser. No. 10/179,938, entitled "Array Assay Devices and Methods of Using the Same", to Shea, et al., filed on even date herewith, the disclosures of which are herein incorporated by reference.

In certain embodiments, the foregoing general assay methods do not include those assay methods described in U.S. application Ser. No. 09/919,073, filed on Jul. 30, 2001.

As mentioned above, in certain embodiments, the subject methods include a step of transmitting data from at least one of the detecting and deriving steps, as described above, to a remote location. By "remote location" it is meant a location other than the location at which the array is present and the array assay, e.g., hybridization, occurs. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

Kits

Finally, kits which include the subject array assay devices are provided. The subject kits at least include one or more subject array assay devices. Typically, a plurality of subject array assay devices is included. The subject kits may also include one or more arrays, for example the subject kits may include one or more arrays and/or one or more substrate receiving frames and/or one or more subject array holders, where the subject arrays may be provided already retained in a subject substrate receiving frame and/or a subject holder. The kits may further include one or more additional components necessary for carrying out an analyte detection assay, such as sample preparation reagents, buffers, labels, and the like. As such, the kits may include one or more containers such as vials or bottles, with each container containing a separate component for the assay, such as an array, and reagents for carrying out an array assay such as a nucleic acid hybridization assay or the like. Thus, the kit may include in packaged combination, an array, wherein the array comprises probes that selectively bind to the detectably labeled target analytes such as detectably labeled target nucleotide sequence, where such arrays may include background probes that do not selectively bind to the target nucleotide sequence and where such arrays may be provided retained in an array holder. The kit may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the subject array assay devices and/or substrate receiving frames and/or array holders and may also include instructions for carrying out the assay. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above results and discussion that the above described invention provides devices and methods for performing array assays which are simple to assemble and use, have minimal components, and can be used with a multitude of different array formats. The above described invention provides for a number of advantages, including fluid loss prevention and the ability to test or assay multiple samples with multiple arrays without cross contamination and. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An array assay device comprising:
    (a) a housing comprising:
        (i) a base comprising an interior surface and an exterior surface and is dimensioned to hold a substrate carrying at least one array;
        (ii) a cover comprising an interior surface and an exterior surface; and
        (iii) a snap-fit attachment for holding said cover and said base together to enclose a space between said interior surface of said cover and said interior surface of said base, wherein the cover is shaped and dimensioned to cover a substrate and an array assay area element held by the base when the base and the cover are snap-fit together; and
    (b) an array assay area element comprising a sealing element and at least one access port, where said array assay area element is dimensioned to cover a substrate comprising a plurality of arrays such that when the base and the cover are snap-fit together, the assay area element is positioned over the substrate and plurality of arrays to provide a substantially vapor and fluid tight assay area around each array of said plurality; and
    (c) an array substrate comprising a plurality of arrays of addressable probe molecules,
    wherein said snap-fit is configured to apply a force to said array substrate and array assay element to hold said substrate and array assay area element together to provide a vapor and fluid tight assay area around each array of said plurality.

2. The array assay device according to claim 1, wherein said snap-fit is a planar snap-fit, a cantilever snap-fit, a torsion snap-fit or an annular snap-fit.

3. The array assay device according to claim 1, wherein said array assay device is substantially vapor and fluid tight when said snap-fit holds said base and said cover together.

4. The array assay device according to claim 1, wherein said enclosed space has a volume of from about 10 μl to about 1000 μl.

5. The array assay device according to claim 1, wherein said base or cover of said array assay device comprises a sealing element for producing a seal around said enclosed space.

6. The array assay device according to claim 5, wherein said seal is substantially vapor and fluid tight.

7. The array assay device according to claim 1, wherein said array assay area element comprises at least a first fluid introduction port and a second venting port.

8. The array assay device according to claim 1, further comprising a substrate receiving frame.

9. The array assay device according to claim 1, further comprising an array holder.

10. The array assay device of claim 5, wherein said snap-fit is configured to apply said force to said sealing element.

11. The array assay device of claim 5, wherein said snap-fit attachment is an integral part of said cover and/or said base.

12. The array assay device of claim 1, further comprising an element that secures said cover to said base on one side to allow said cover to move between an opened and a closed position In relation to said base.

13. The array assay device of claim 12, wherein said securing element is a hinge.

14. A kit for performing an assay, said kit comprising:
(a) at least one array assay device according to claim 1; and
(b) instructions for using said at least one array assay device.

15. The kit according to claim 14, further comprising at least one array holder.

16. The kit according to claim 14, further comprising reagents for generating a labeled sample.

17. The kit according to claim 14, wherein said kit further comprises a buffer.

18. The kit according to claim 14, wherein said kit further comprises a wash medium.

19. An array assay device comprising:
(a) an array substrate comprising at least one array of addressable probe molecules;
(b) an array assay area element having at least one access port and a sealing element around the array assay area, wherein said array assay area element is dimensioned to provide a substantially vapor and fluid tight assay area around each of a plurality of arrays of said substrate when positioned over said substrate; and
(c) a housing comprising:
(i) a base comprising an interior surface and an exterior surface;
(ii) a cover comprising an interior surface and an exterior surface; and
(iii) a snap-fit attachment for holding said cover and said base together to enclose a space between said interior surface of said cover and said interior surface of said base that is dimensioned to hold the substrate and array assay area element by a force that is sufficient to provide a vapor and fluid tight assay area around said at least one array;
wherein said array assay substrate and array assay area element are not attached to said cover or base.

20. The array assay device according to claim 19, wherein said snap-fit is a planar snap-fit, a cantilever snap-fit, a torsion snap-fit or an annular snap-fit.

* * * * *